United States Patent [19]

Spencer

[11] Patent Number: 4,987,785
[45] Date of Patent: Jan. 29, 1991

[54] CONSTANT VOLUME SAMPLING SYSTEM

[76] Inventor: R. Wilson Spencer, P.O. Box 22586, Houston, Tex. 77227-2586

[21] Appl. No.: 505,051

[22] Filed: Apr. 4, 1990

[51] Int. Cl.$^5$ .......................... G01N 1/18; G01N 1/28
[52] U.S. Cl. .............................. 73/863.71; 73/863.61; 73/863.86; 436/174
[58] Field of Search ................ 73/863.71, 863.86, 863, 73/863.61, 863.81–863.86, 864.83, 864.63, 864, 863.72, 863.73, 863.31, 863.32, 863.33, 864.73, 864.74; 436/174

[56] References Cited

U.S. PATENT DOCUMENTS

| | | |
|---|---|---|
| 1,837,858 | 12/1931 | Grace . |
| 2,434,723 | 1/1948 | Shook . |
| 3,083,577 | 4/1963 | Nelson et al. . |
| 3,369,405 | 2/1968 | Galegar ........................ 73/863.86 X |
| 3,429,186 | 2/1969 | Price et al. ........................ 73/863.61 |
| 3,638,498 | 2/1972 | Nelms . |
| 4,174,632 | 11/1979 | Jansen . |
| 4,628,749 | 12/1986 | Rafter, Jr. ........................ 73/863.71 |
| 4,651,574 | 3/1987 | Spencer ....................... 73/864.74 X |
| 4,658,655 | 4/1987 | Kanno .............................. 73/863.85 |
| 4,712,434 | 12/1987 | Herwig et al. ................... 73/864.63 |
| 4,750,941 | 6/1988 | Gerich ........................ 73/863.61 X |
| 4,755,357 | 7/1988 | Noguchi et al. ..................... 422/103 |
| 4,791,821 | 12/1988 | Spencer ........................... 73/864.74 |
| 4,800,761 | 1/1989 | Spencer ........................... 73/863.71 |
| 4,823,622 | 4/1989 | Nohl et al. ...................... 73/863.71 |
| 4,879,915 | 11/1989 | Spencer ........................... 73/864.74 |

Primary Examiner—Tom Noland
Attorney, Agent, or Firm—Robert C. Tucker; William David Kiesel

[57] ABSTRACT

A constant volume sampling system is provided, comprising a sample loop including a section of tubing having a predetermined volume and having a first end and a second end; a first valve having a first port, connectable to a process line, a second port connected to the first end of the sample loop, a third port, connectable to a pressurized gas line, and a selector for selectively establishing flow between the first and second ports or between the second and third ports; a second valve having a first port, connectable to the process line, a second port, connected to the second end of the sample loop, a third port, connectable to a sample container, and a selector for selectively establishing flow between the first and second ports or between the second and third ports; an actuator, for operating the first valve and the second valve; and a linkage, for linking the actuator and the first and second valves such that the actuator operates the first and second valves simultaneously, the linkage being operably connected externally of the sample loop to the first valve, the second valve and the actuator. A method is provided for operating the system so as to neutralize a hazardous sample as it is taken by placing a neutralizing substance in the sample container before the sample is taken.

15 Claims, 6 Drawing Sheets

CONSTANT VOLUME SAMPLING SYSTEM

BACKGROUND OF THE INVENTION

1. Field of the Invention

This invention relates generally to sampling systems which remove a sample from a process line containing a flowing fluid and, more particularly, to sampling systems which remove a specified volume of fluid from a process line.

2. Prior Art

There are many types of devices which remove samples from process lines. R. Wilson Spencer's prior U.S. Pat. Nos. 4,651,574, 4,791,821, 4,800,761 and 4,879,915 are examples of such devices. In specialized situations, often having a specified volume, with each successive sample having the same specified volume. It is tedious and sometimes dangerous to measure a specific volume of fluid into a sample container using standard sampling systems. In the case of hazardous fluid sampling, it is usually desirable to obtain a sample having a very small volume in order to limit exposure to the substance as well as limit the amount of neutralizing substance which must be added to the sample for safe handling in the lab.

In order to meet the sampling criteria set out above, prior art samplers have used a pair of three-way valves which are connected by a sample cylinder. One valve is connected to the process line and a pressurized gas source, usually an inert gas such as nitrogen. The second valve is connected to the process line and to a vented sample container. The operational parts of the valves are connected through the sample cylinder by a rotatable shaft which allows the valves to be operated simultaneously. Thus, a flow is established from the process line through the sample cylinder and back to the process line. Manipulation of the valves shuts off the flow from the process line, trapping a sample in the cylinder. Further operation of the valves allows the sample to be ejected from the cylinder by the pressurized gas into the sample container. The container is then removed and taken to a lab for analysis (and neutralization, if hazardous).

Prior art samplers do not facilitate easy changing of sample volumes. For example, if the operator desires to change from a 100 cc sample volume to a 50 cc sample volume, the sample cylinder and shaft (which is connected through the cylinder) must be removed requiring complete disassembly of the sampling system. Further, as the desired sample volume decreases, it is difficult to find standard sample cylinders haVing such small volumes which also have room for the internal shaft connecting the two valves. In addition to the above problems, cleaning of the prior art systems is impossible without disassembly, and the shaft is contaminated during operation. Also, plugging of the sample passageways is possible due to the restrictions caused by the narrow clearance of the shaft within the cylinder, as well as shaft connections within the valves.

SUMMARY OF THE INVENTION

Therefore, it is an object of this invention to provide a constant volume sampling system which separates the linkage between valves from the passageways which transmit sample flow.

It is another object of this invention to provide a constant volume sampling system which allows for easy changing of sample volumes.

It is still another object of this invention to provide a constant volume sampling system which will handle small volume samples.

It is a further object of this invention to provide a constant volume sampling system which is compact, simple to operate and easy to clean.

It is a further object of this invention to provide a constant volume sampling system in accordance with the above objects and which is remotely operable.

It is another object of this invention to provide a constant volume sampling system which allows the operator to neutralize the sample as it is being taken, without exposure to the operator.

Accordingly, a constant volume sampling system is provided, comprising a sample loop including a section of tubing having a predetermined volume and having a first end and a second end; a first valve having a first port, connectable to a process line, a second port connected to the first end of the sample loop, a third port, connectable to a pressurized gas line, and a selector for selectively establishing flow between the first and second ports or between the second and third ports; a second valve having a first port, connectable to the process line, a second port, connected to the second end of the sample loop, a third port, connectable to a sample means, and a selector for selectively establishing flow between the first and second ports or between the second and third ports; an actuator, for operating the first valve and the second valve; and a linkage, for linking the actuator and the first and second valves such that the actuator operates the first and second valves simultaneously, the linkage being operably connected externally of the sample loop to the first valve, the second valve and the actuator. A method is provided for operating the system so as to neutralize a hazardous sample as it is taken by placing a neutralizing substance in the sample container before the sample is taken.

DETAILED DESCRIPTION OF PREFERRED EMBODIMENTS OF THE INVENTION

As shown in the Figures, the invention 1 includes several basic parts. The sampling operation is accomplished using two three-way valves, such as the Hoke Model 7165 F4Y three-way ball valve or equivalent. A first valve 2 is connected to a process line (not shown) via inlet process tap line 3, to a pressurized gas line 4 and to a sample loop 5. A second valve 6 is connected to the process line via outlet process tap line 7, to a sample means 8, for receiving a sample, and to sample loop 5. Actuator means 9 allows first valve 2 and second valve 6 to be operated simultaneously, via linkage means 10, which operates externally of sample loop 5.

Figure 1:
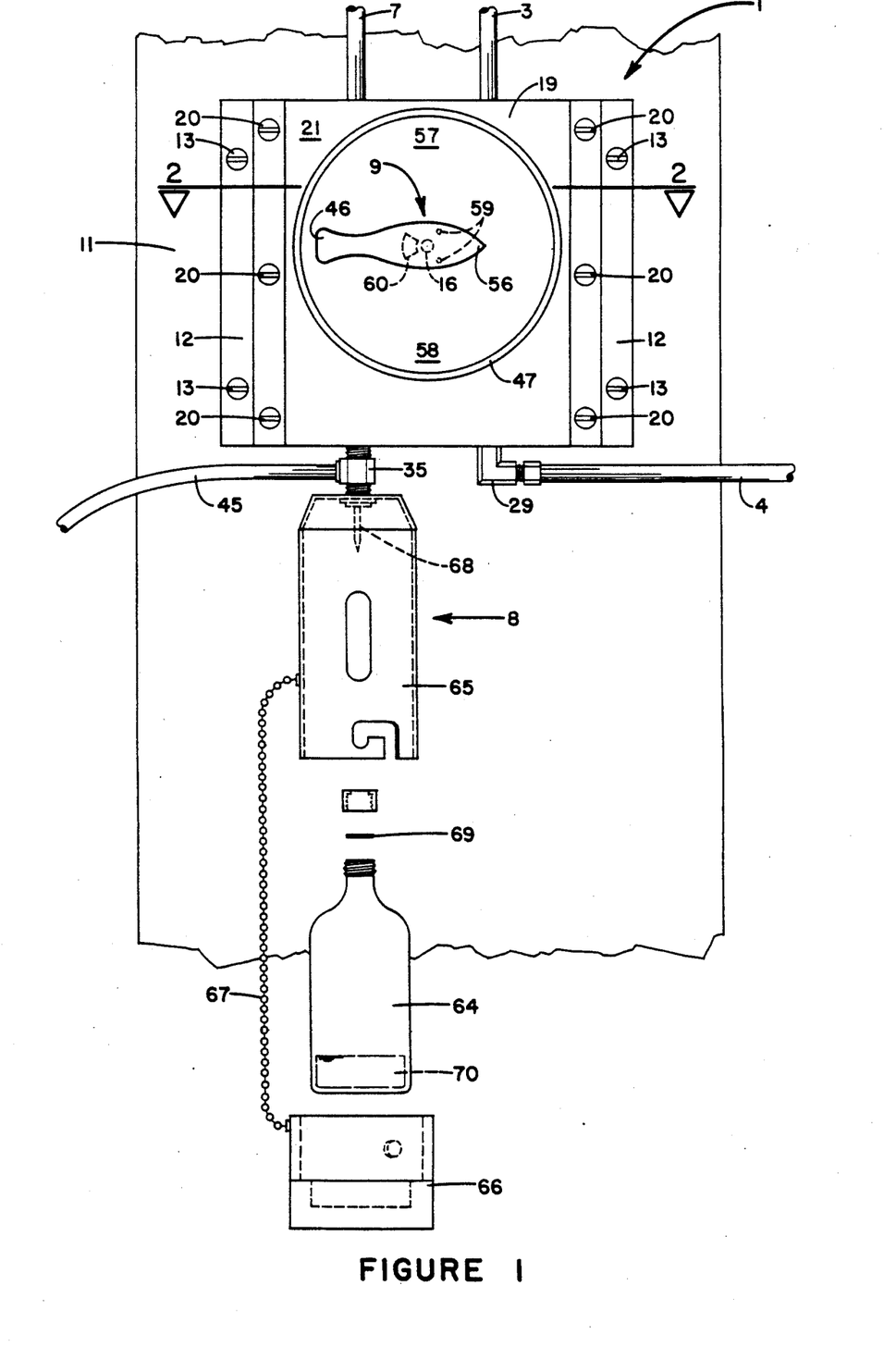
FIG. 1 is a front view of an embodiment of the invention.
Figure 2:
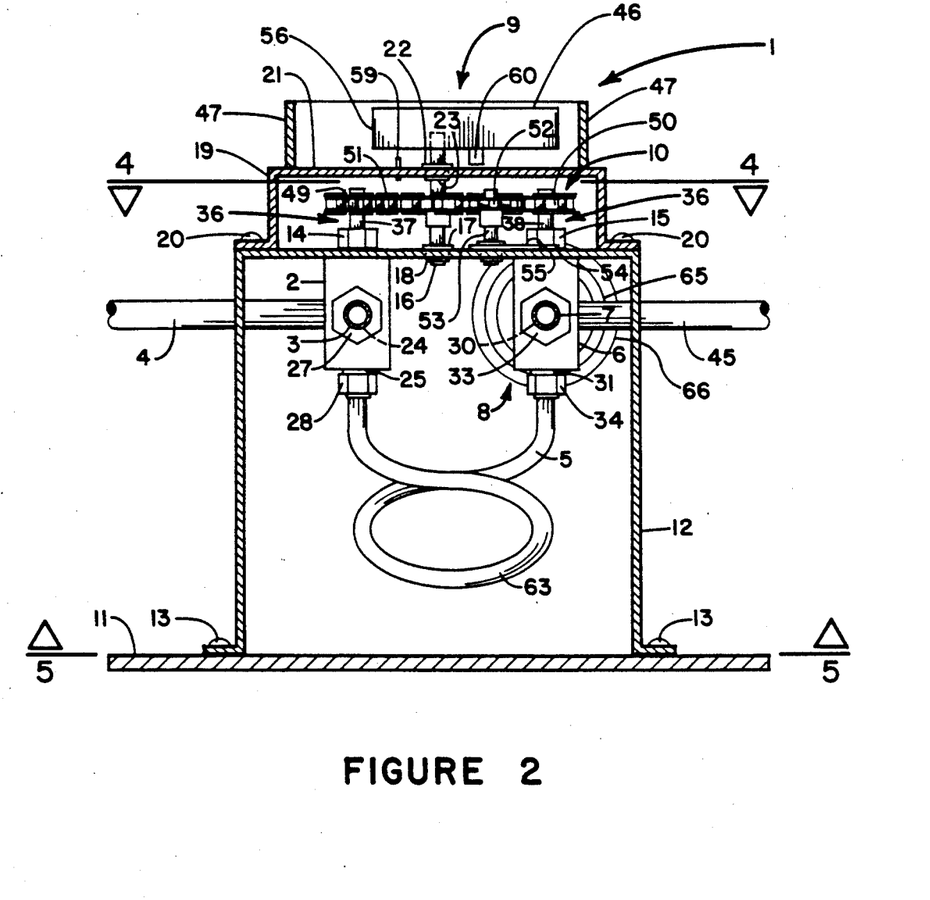
FIG. 2 is a sectional top view of the invention taken along line 2-2 of FIG. 1.

The system 1 is preferably installed on a fixed surface 11 near the point where the process line is tapped. A mounting bracket 12 is attached to fixed surface 11, as shown in FIGS. 1 and 2, by mounting bracket screws 13 or bonded by other means such as welding. As shown in FIG. 2, mounting bracket 12 can have a channel shape so as to encase and protect valves 2 and 6 as well as sample loop 5. Valves 2 and 6 are mounted through holes in mounting bracket 12 and held in place by first valve nut 14 and second valve nut 15. Actuator means 9 is also attached to mounting bracket 12. When actuator means 9 is equipped with actuator stem 16, actuator stem 16 is rotatably mounted in bearing 17 on mounting bracket 12, and is held in place by snap ring 18. Additional protection of components is provided by face bracket 19, which is attached to mounting bracket 12 by face bracket screws 20 or other bonding means such as welding. Face bracket 19 protects and encases linkage means 10, and provides a surface 21 on which the position of actuator means 9 may be indicated. Actuator stem 16 is also rotatably mounted in bearing 22 on face bracket 19, and is held in place by snap ring 23.

First valve 2 has a first port 24 connectable to inlet process tap line 3 at fitting 27; a second port 25 connected to sample loop 5 at fitting 28; and a third port 26 connectable to pressurized gas line 4 at fitting 29. Likewise, second valve 6 has a first port 30 connectable to outlet process tap line 7 at fitting 33; a second port 31 connected to sample loop 5 at fitting 34 and a third port 32 connectable to sample means 8 at fitting 35. Each valve 2,6 has a selector means 36 for selectively establishing flow between first port 24,30 and second port 25,31 or between second port 25,31 and third port 26,32. Selector means 36 includes the typical inner workings of the three-way ball valves 2,6 described above, operated by valve stems 37 and 38. However, other types of valves and selector means known in the art may suffice, so long as the flow is directed as described herein.

Figure 6:
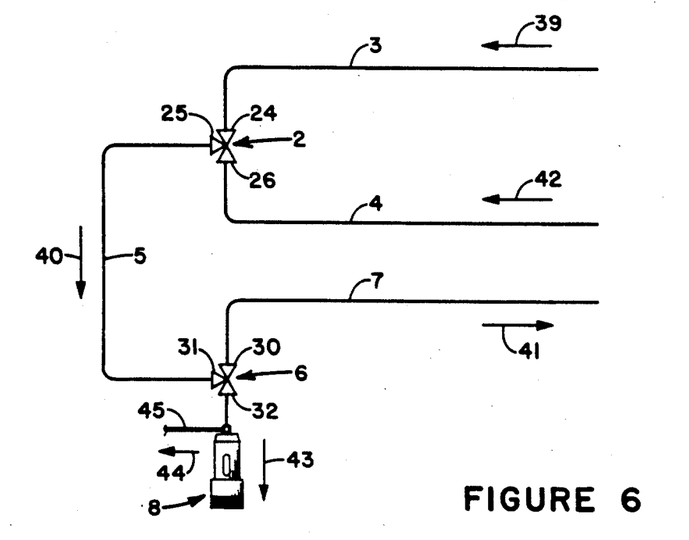
FIG. 6 is a schematic depiction of the invention.

Thus, when valve stem 37 is turned, first valve 2 will move from a first position connecting inlet process tap line 3 and sample loop 5 to a second position connecting pressurized gas line 4 and sample loop 5. When valve stem 38 is turned, second valve 6 will move from a first position connecting outlet process tap line 7 and sample loop 5 to a second position connecting sample means 8 and sample loop 5. FIG. 6 schematically illustrates the flow induced by the various positions of valves 2 and 6 utilizing flow arrows 39-44. When valves 2,6 are in the first position described above, the fluid flow follows flow arrows 39, 40 and 41, establishing a representative flowing sample in sample loop 5. As valves 2,6 are moved to the second position, a sample of the process fluid is first trapped in sample loop 5. Then, as valves 2, 6 reach the second positions, pressurized gas pushes the sample from sample loop 5 into sample means 8, with the gas being vented through vent line 45, the flow following flow arrows 42, 40, 43 and 44.

It is necessary that both valves 2,6 operate simultaneously in order to properly eject a sample into sample means 8. Actuator means 9 and linkage means 10 accomplish this task. The key is to move the valves 2,6 between first and second positions externally of sample loop 5 in order to eliminate prior art linkages. Preferred embodiments of actuator means 9 and linkage means 10 are shown in FIGS. 1-5. As shown in FIGS. 1 and 2, actuator means 9 may comprise an actuator stem 16, rotatably attached to mounting bracket 12 and face bracket 19, and an actuator handle 46, fixedly attached to stem 16 outside of face bracket 19. Flange 47 extends from face bracket 19 to protect handle 46.

Figure 4:
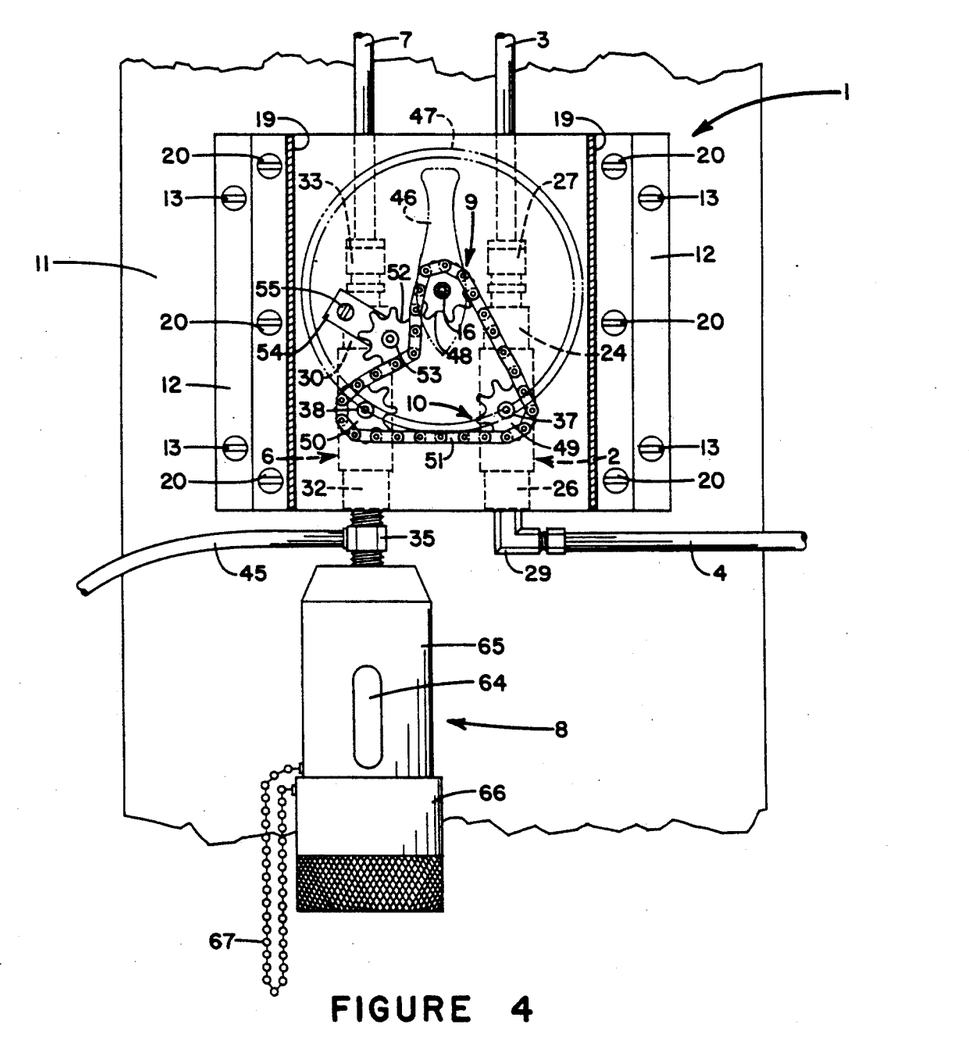
FIG. 4 is a sectional view of the invention taken along line 4-4 of FIG. 2.
Figure 5:
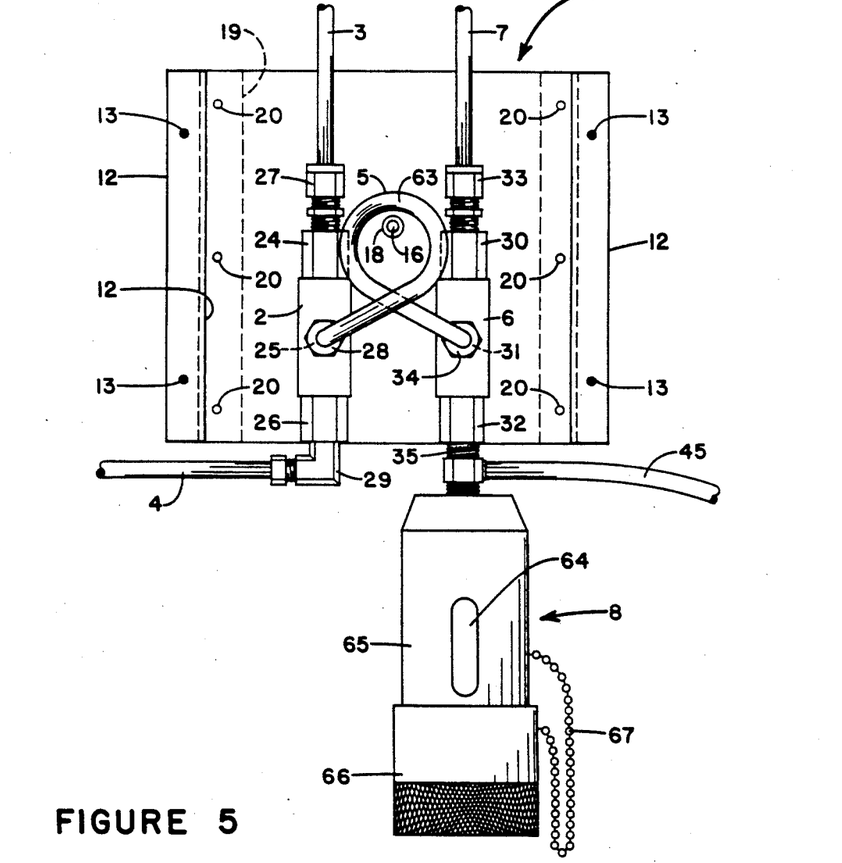
FIG. 5 is a sectional back view of the invention taken along line 5-5 of FIG. 2.

Linkage means 10 is shown in detail in FIG. 4, and preferably includes a chain drive arrangement which allows valves 2,6 to be operated by actuator means 9 externally of sample loop 5. A first sprocket 48 is fixedly attached to actuator stem 16 between mounting bracket 12 and face bracket 19. A second sprocket 49 is fixedly attached to valve stem 37 of first valve 2 in the same plane as first sprocket 48. A third sprocket 50 is fixedly attached to valve stem 38 of second valve 6 in the same plane as first sprocket 48. Chain 51 is operably attached around sprockets 48, 49 and 50, as shown. Tension on chain 51 is maintained by idler sprocket 52, which is rotatably attached to idler stem 53. Idler stem 53 is fixedly attached to idler plate 54. Idler plate is pivotally attached to mounting bracket 12 by idler screw 55. Sprockets 48, 49 and 50 should be the same size, such that movement of chain 51 will exert simultaneous, identical rotation of valve stems 37 and 38.

Figure 7:
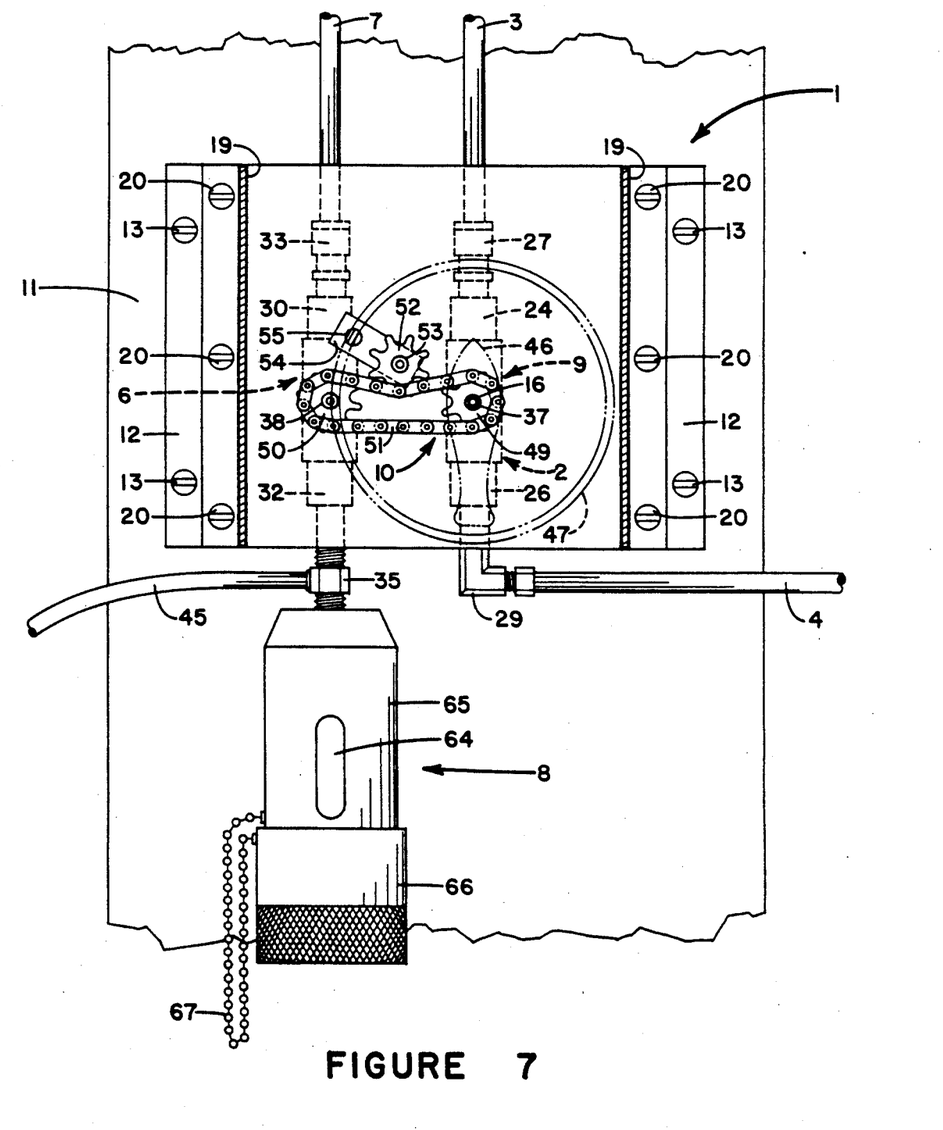
FIG. 7 is the same view as FIG. 4, but of an alternate embodiment of the invention in which the selector means of one valve includes the actuator means of the invention.

As shown in FIG. 7, actuator means 9 may be included as part of one selector means 36 of one of the valves 2, 6. As shown, valve stem 37 of valve 2 can extend through face bracket 19, and handle 46 attached thereto. Thus, chain 51 attaches to sprockets 49, 50 and 52 only, eliminating the need for a separate sprocket 48 for actuator means 9. However, this embodiment may not prove as versatile when it is necessary to service valves 2, 6 frequently, since disassembly of valve 2 from face bracket 19 is required.

In order to calibrate the system 1, valves 2,6 are adjusted to the first position described above. Idler sprocket 52 is urged against chain 51 and idler screw 55 is tightened, thus maintaining chain tension. Rotation of handle 46 will now rotate valve stems 37,38. In the embodiment shown in FIG. 1, the pointer 56 of handle 46 is between first position, denoted by the number 57 and second position, denoted by the number 58. In practice, face bracket 19 should be marked with terms such as "CIRCULATE" at first position 57 and "SAMPLE" at second position 58. Stop pins 59 extend outward from face bracket 19. Handle stop 60 extends inward from handle 46 toward face bracket 19. Stop pins 59 are positioned such that handle stop 60 will strike them and stop handle rotation when handle 46 reaches first position 57 or second position 58.

Figure 3:
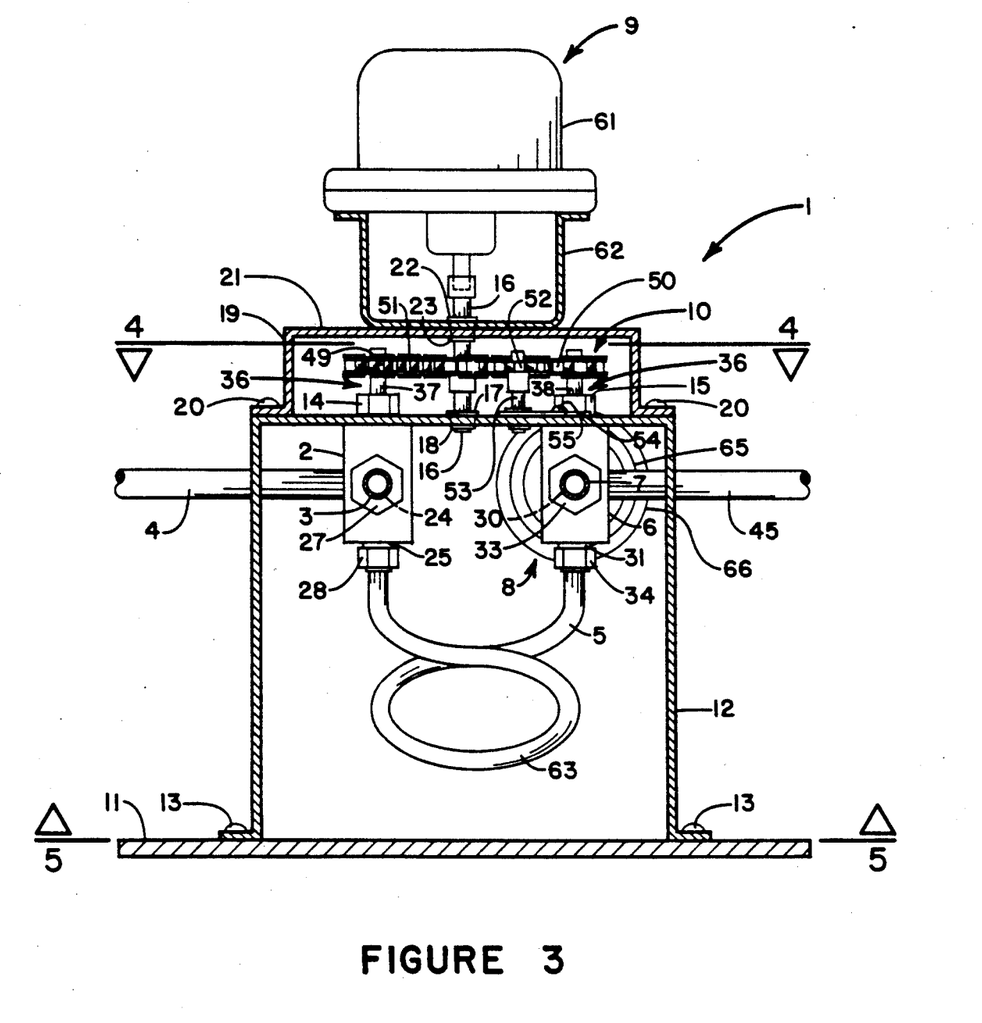
FIG. 3 is the same view as FIG. 2, but of an alternate embodiment of the invention having a remote valve actuator.

An alternate embodiment of the system 1 is shown in FIG. 3, wherein handle 46 is replaced by a remote valve actuator 61, fixedly attached to face bracket 19 by mounting hardware 62, which will automatically rotate actuator stem 16 between first position 57 and second position 58. Remote actuator 61 may take any form known in the art, such as the Hoke Selectomite valve actuator, part number 0112Y6F. Actuator means 9 could include dual remote actuators 61 (not shown) connected to valves 2, 6. In such a situation, linkage means 10 could comprise electronic, pneumatic or other types of linkages between valves 2, 6.

Sample loop 5 is sized to provide an accurate sample size, and includes a section of tubing 63, as shown. The tubing 63 may be made of metal, plastic or other material as dictated by sampling needs. The use of tubing 63 allows for a great deal of flexibility in sample size and space considerations. As shown, tubing 63 is looped to conserve space. The looped arrangement of sample loop 5 allows relatively large samples to be obtained if desired. Of course, for very small samples, a short, small diameter piece of tubing 63 can be installed, eliminating the need for special sample cylinders. Tubing 63 is easily and quickly changeable by simply uncoupling fittings 28 and 3 and replacing sample loop 5.

Sample means 8 may take any form known in the art. The arrangement shown is described in greater detail in U.S. Pat. No. 4,651,574. The sample flows through fitting 35 into sample container 64. Shroud 65 and shroud base 66 protect the container 64 from breakage. Safety chain 67 prevents loss of shroud base 66. In the embodiment shown, an integral vented needle 68 is included in fitting 35. Needle 68 pierces a septum 69 at the top of container 64 when container 64 is installed. Needle 68 has two passageways. One is connected through fitting 35 to third port 32 of second valve 6, and conducts fluid into container 64. The other passageway is connected through fitting 35 to vent line 45. Thus, when a sample is forced into container 64 by pressurized gas, the gas is vented through vent line 45. An absorber (not shown) or gas trap (not shown) may be added to vent line 45 for environmental protection. Of course, the type of sample means 8 shown is only an example. Any suitable container known in the art may be used with the system 1.

Operation of the system 1 is simple. The system 1 is installed as described above. Inlet process tap line 3 and outlet process tap line 7 are connected to a process line (not shown) at points such that the pressure at tap line 3 is greater than that at tap line 7, in order to establish flow through the system. Typical locations are on either side of an orifice plate or pump. Also, a pump could be installed in either tap line 3,7 in order to create flow in the system 1. Once the system 1 is installed and with the system in first position 57, a sample means 8 is connected to sample fitting 35. Actuator means 9 is then moved to second position 58. The sample from sample loop 5 is discharged into sample means 8. Actuator means 9 is returned to first position 57, and sample container 64 is removed from sample means 8 and taken to the lab.

For sampling of hazardous substances requiring neutralization, such as phosgene, a neutralizing substance 70 is placed in sample means 8 prior to sampling. Since the volume of the sample is known, the proper volume of neutralizing substance 70 can be premeasured. When the sample is taken, it is therefore immediately neutralized without exposure to personnel and without danger of exposure during transportation to the lab, even if sample container 64 is dropped and broken.

As can be seen, a constant volume sampling system is described herein which provides a simple and efficient way to obtain a homogeneous sample of a desired volume. The linkage means 10 of the system 1 is not contaminated by the sample being taken. Sample volume can be changed quickly and easily by changing sample loop 5. The system 1 is compact and easy to install, and can be operated remotely. A neutralizing substance 70 can be put into the sample container 64 prior to sampling to assure safety. Many other embodiments of the invention will occur to those skilled in the art, and are intended to be included within the scope and spirit of the following claims.

I claim:

1. A constant volume sampling system, comprising:
   a. a sample loop including a section of tubing having a predetermined volume and having a first end and a second end;
   b. a first valve having a first port, connectable to a process line at a first point, a second port connected to said first end of said sample loop, a third port, connectable to a pressurized gas line, and a selector means for selectively establishing flow between said first and second ports or between said second and third ports;
   c. a second valve having a first port, connectable to said process line at a second point wherein the pressure in said process line is less than the pressure at said first point, a second port, connected to said second end of said sample loop, a third port, connectable to a sample means for receiving a sample, and a selector means for selectively establishing flow between said first and second ports or between said second and third ports;
   d. an actuator means, for operating said first valve and said second valve; and
   e. a linkage means, for mechanically linking said actuator means and said first and second valves such that said actuator means operates said first and second valves simultaneously, said linkage means being operable connected externally of said sample loop to said first valve, said second valve and said actuator means.

2. A constant volume sampling system according to claim 1, wherein said linkage means includes a first sprocket operably connected to said actuator means, a second sprocket operably connected to said selector means of said first valve, a third sprocket operably connected to said selector means of said second valve, and a chain, operably connected to said first sprocket, said second sprocket and said third sprocket.

3. A constant volume sampling system according to claim 2, further comprising:
   f. a mounting bracket, fixedly connected to said first valve and said second valve.

4. A constant volume sampling system according to claim 3, wherein said selector means of said first valve includes a first valve stem and said selector means of said second valve includes a second valve stem and said actuator means includes an actuator stem, and wherein said first sprocket is fixedly attached to said first valve stem and said second sprocket is fixedly attached to said second valve stem and said third sprocket is fixedly attached to said actuator stem.

5. A constant volume sampling system according to claim 4, wherein said actuator stem is rotatably connected to said mounting bracket.

6. A constant volume sampling system according to claim 5, wherein said actuator means includes a handle mounted on said actuator stem.

7. A constant volume sampling system according to claim 5, further comprising:
   g. a face bracket, fixedly connected to said mounting bracket so as to encase said linkage means, said face bracket including an opening through which said actuator stem passes.

8. A constant volume sampling system according to claim 7, wherein said actuator means includes a handle mounted on said actuator stem exterior of said face bracket.

9. A constant volume sampling system according to claim 8, further comprising:
   h. a handle stop, fixedly attached to and extending from said handle toward said face bracket;
   i. a first position stop, fixedly attached to said face bracket and extending toward said handle to a point wherein said first position stop will block movement of said handle stop when said handle is in a desired first position; and j. a second position stop, fixedly attached to said face bracket and extending toward said handle to a point wherein said second position stop will block movement of said handle stop when said handle is in a desired second position.

10. A constant volume sampling system according to claim 7, wherein said actuator means further includes a remote valve actuator, operably connected to said actuator stem.

11. A constant volume sampling system according to claim 1, further comprising:
   f. a mounting bracket, fixedly connected to said first valve and second valve.

12. A constant volume sampling system according to claim 1, further comprising:
   f. a sample means for receiving a sample, connectable to said third port of said second valve, and wherein said sample means includes a sample container with a neutralizing substance contained therein.

13. A constant volume sampling system according to claim 1 wherein said selector means of said first valve includes said actuator means.

14. A constant volume sampling system according to claim 1 wherein said selector means of said second valve includes said actuator means.

15. In a constant volume sampling system, comprising:
   a. a sample loop including a section of tubing having a predetermined volume and having a first end and a second end;
   b. a first valve having a first port, connected to a process line at a first point, a second port connected to said first end of said sample loop, a third port, connected to a pressurized gas line, and a selector means for selectively establishing flow between said first and second ports or between said second and third ports;
   c. a second valve having a first port, connectable to a process line at a second point wherein the pressure in said process line is less than the pressure at said first point, a second port, connected to said second end of said sample loop, a third port, connected to a sample means for receiving a sample, and a selector means for selectively establishing flow between said first and second ports or between said second and third ports;
   d. an actuator means, for operating said first valve and said second valve;
   e. a linkage means, for linking said actuator means and said first and second valves such that said actuator means operates said first and second valves simultaneously, said linkage means being operably connected externally of said sample loop to said first valve, said second valve and said actuator; and
   f. a sample means for receiving a sample, connected to said third port of said second valve, said sample container having a neutralizing substance contained therein;

a method for gathering a sample of a hazardous fluid flowing in said process line, comprising the steps of:
   a. positioning said actuator means in a first position so as to establish flow of said fluid from said first point in said process line through said sample loop to said second point in said process line; and moving said actuator means to a second position thereby trapping a sample of said fluid in said sample loop and allowing pressurized gas from said pressurized gas line to force said sample from said sample loop into said neutralizing substance in said sample means.

* * * * *